(12) United States Patent
Villain et al.

(10) Patent No.: US 11,672,603 B2
(45) Date of Patent: Jun. 13, 2023

(54) SYSTEM FOR PATIENT-SPECIFIC INTERVENTION PLANNING

(71) Applicant: KONINKLIJKE PHILIPS N.V., Eindhoven (NL)

(72) Inventors: Nicolas François Villain, Rueil-Malmaison (FR); Hernan Guillermo Morales Varela, Suresnes (FR); Mathieu De Craene, Suresnes (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 412 days.

(21) Appl. No.: 16/911,918

(22) Filed: Jun. 25, 2020

(65) Prior Publication Data
US 2021/0059755 A1  Mar. 4, 2021

Related U.S. Application Data

(60) Provisional application No. 62/893,238, filed on Aug. 29, 2019.

(51) Int. Cl.
*G16H 30/40* (2018.01)
*G16H 50/50* (2018.01)
(Continued)

(52) U.S. Cl.
CPC .............. *A61B 34/10* (2016.02); *B33Y 10/00* (2014.12); *B33Y 50/02* (2014.12); *B33Y 80/00* (2014.12);
(Continued)

(58) Field of Classification Search
CPC .... A61B 2017/00707; A61B 2034/105; A61B 2034/2051; A61B 2034/2055;
(Continued)

(56) References Cited

U.S. PATENT DOCUMENTS 8,121,859 B2   2/2012   Becker et al.
8,744,870 B2   6/2014   Agnihotram et al.
(Continued)

FOREIGN PATENT DOCUMENTS

WO   2017024346 A1   2/2017

OTHER PUBLICATIONS

Brouwers et al., Validation study of 3D-printed anatomical models using 2 PLA printers for preoperative planning in trauma surgery, a human cadaver study, 2018, European Journal of Trauma and Emergency Surgery p. 1013-1020. (Year: 2018) (Year: 2018).*

(Continued)

*Primary Examiner* — Kidest Bahta

(57) ABSTRACT

The present disclosure relates to a system for patient-specific intervention planning, the system comprising a physical model of an anatomical structure, wherein the physical model is a patient-specific model based on medical image data; a virtual model of the anatomical structure, wherein the virtual model is a patient-specific model based on medical image data; a tracking device configured to track a position of a physical representation of an interventional tool with respect to the physical model of the anatomical structure; a processor configured to perform the step of: registering the physical model of the anatomical structure with the virtual model of the anatomical structure and registering the physical representation of the interventional tool with a virtual representation of the interventional tool based on the position of the physical representation of the interventional tool and the physical model of the anatomical structure. The present disclosure further relates to a corresponding method and computer program.

15 Claims, 4 Drawing Sheets

(51) Int. Cl.
*A61B 34/10* (2016.01)
*G16H 40/67* (2018.01)
*G16H 20/40* (2018.01)
*G05B 19/4099* (2006.01)
*B33Y 10/00* (2015.01)
*B33Y 50/02* (2015.01)
*B33Y 80/00* (2015.01)
*G16H 30/20* (2018.01)
*A61B 34/20* (2016.01)
*A61B 90/00* (2016.01)
*G06Q 50/04* (2012.01)
*B22F 10/00* (2021.01)

(52) U.S. Cl.
CPC ......... *G05B 19/4099* (2013.01); *G16H 20/40* (2018.01); *G16H 30/20* (2018.01); *G16H 30/40* (2018.01); *G16H 40/67* (2018.01); *G16H 50/50* (2018.01); *A61B 2034/105* (2016.02); *A61B 2034/2051* (2016.02); *A61B 2090/374* (2016.02); *A61B 2090/378* (2016.02); *A61B 2090/3762* (2016.02); *B22F 10/00* (2021.01); *G05B 2219/35134* (2013.01); *G05B 2219/49023* (2013.01); *G06Q 50/04* (2013.01)

(58) Field of Classification Search
CPC ........ A61B 2090/365; A61B 2090/372; A61B 2090/374; A61B 2090/3762; A61B 2090/378; A61B 2090/502; A61B 34/10; B33Y 10/00; B33Y 50/02; B33Y 80/00; B22F 10/00; B22F 12/00; G06Q 50/04; G09B 23/28; G09B 23/30; G09B 5/00; G16H 20/40; G16H 30/20; G16H 30/40; G16H 40/67; G16H 50/50; G16H 10/00; G06T 2200/04; G06T 19/003; G06T 19/20; G06T 2200/08
See application file for complete search history.

(56) References Cited

U.S. PATENT DOCUMENTS

| | | | | |
|---|---|---|---|---|
| 2013/0323700 | A1* | 12/2013 | Samosky | G09B 23/30 434/262 |
| 2014/0306918 | A1* | 10/2014 | Groth | G09B 23/28 345/173 |
| 2015/0049081 | A1* | 2/2015 | Coffey | G06T 19/006 345/419 |
| 2015/0254408 | A1 | 9/2015 | Dadlani et al. | |
| 2016/0155236 | A1* | 6/2016 | Davey | G06T 15/08 382/131 |
| 2016/0253473 | A1 | 9/2016 | Anderson et al. | |
| 2017/0057175 | A1* | 3/2017 | Blackmon | B33Y 50/02 |
| 2017/0372640 | A1* | 12/2017 | Lampotang | G09B 9/00 |
| 2018/0001581 | A1* | 1/2018 | Patel | B29D 11/00961 |
| 2019/0021865 | A1* | 1/2019 | Vogtmeier | A61F 2/30942 |
| 2019/0271967 | A1 | 9/2019 | Mora et al. | |

OTHER PUBLICATIONS

Souza, K.D. The SIMULIA Living Heart Model. Dassault Systemes, Nafems Benchmark Jul. 2015.
Chabiniok, R. et al., "Multiphysics and multiscale modelling, data—model fusion and integration of organ physiology in the clinic: ventricular cardiac mechanics". The Royal Society Publishing (Aug. 9, 2018).
Scoles, S. "A digital twin of your body could become a critical part of your health care". SLATE, Feb. 10, 2016.

* cited by examiner

SYSTEM FOR PATIENT-SPECIFIC INTERVENTION PLANNING

FIELD OF THE INVENTION

The present invention relates to the field of medical technology and in particular to a system and method patient-specific intervention planning as well as to a corresponding computer program.

BACKGROUND OF THE INVENTION

Printed organs are becoming more and more relevant for interventional planning and training.

Physicians at the University of Rochester Medical Center (URMC) suggest to fabricate artificial organs and human anatomy that mimic the real organ, even up to the point of bleeding when cut. The process entails converting images obtained from medical scans into computer generated designs and, through the assistance of 3D printing, fabricating lifelike organs that can be poked, prodded, and dissected.

A potential application scenario is to use such physical models for training and to rehearse complex cases prior to surgery, i.e., before the patient is brought into the operating room. This may help to eliminate the unknown, increases safety, and improve the quality of care.

The company Biomodex, suggests using 3D printing to create tissue-like anatomical physical models from medical images, for patient-specific rehearsal and advanced training. The physical model is designed to provide tactile feedback to users. The physical model can be connected to a pumping station that provides a simulated blood flow. WO 2018/051162 A1 by Biomodex discloses a respective physical simulation device, a method for fabricating the same and a simulation system. The disclosure relates to physical simulation devices able to mimic the physical behavior of a complex object, such as an artery, having a complex mechanical behavior.

The company SiMMO3D proposes a medical training platform called Simuboard that shall allow a surgeon to practice implantation techniques. The training platform supports a water-tight pumping system that pulsates to a heartbeat as it circulates fluid trough the physical model during a surgical training session. A modular design with disposable sections is proposed. The modular design shall allow quick removal and replacement of disposable sections.

SUMMARY OF THE INVENTION

It is an object of the present invention to provide a system that may further reduce the cost of patient-specific intervention planning with printed organs.

In a first aspect of the present invention a system for patient-specific intervention planning is presented. The system for use in patient-specific intervention planning comprises:

a physical model of an anatomical structure, wherein the physical model is a patient-specific physical model created based on medical image data;

a virtual model of the anatomical structure, wherein the virtual model is a patient-specific virtual model created based on medical image data;

a tracking device configured to track a position of a physical representation of an interventional tool and the physical model of the anatomical structure;

a processor configured to perform the step of registering the physical model of the anatomical structure with the virtual model of the anatomical structure and registering the physical representation of the interventional tool with a virtual representation of the interventional tool, possibly performing the latter based on the position of the physical representation of the interventional tool and the physical model of the anatomical structure, in particular based on an interaction of the representation of the interventional tool with the physical model of the anatomical structure.

In a further aspect of the present disclosure a method for patient-specific intervention planning is presented, the method comprising:

receiving medical image data;

generating a physical model of an anatomical structure, wherein the physical model is a patient-specific physical model, based on the medical image data;

generating or determining a virtual model of the anatomical structure, wherein the virtual model is a patient-specific virtual model based on the medical image data;

providing a physical representation of an interventional tool;

tracking a position of the physical representation of the interventional tool and the physical model of the anatomical structure; and registering the physical model of the anatomical structure with the virtual model of the anatomical structure and registering the physical representation of the interventional tool with a virtual representation of the interventional tool based on the position of the physical representation of an interventional tool and the physical model of the anatomical structure.

In yet further aspects of the present invention, there are provided a corresponding a computer program which comprises program code means for causing a computer to perform the steps of the method disclosed herein when said computer program is carried out on a computer, insofar as they can be implemented in program code means, as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, computer program and medium have similar and/or identical preferred embodiments as the claimed system, in particular as defined in the dependent claims and as disclosed herein.

The inventors have recognized that printing an organ is expensive and therefore, reusability would be highly desirable. The present disclosure can allow reusability based on a combination of a physical model of a patient-specific anatomical structure with a virtual model of the patient specific anatomical structure. The physical model of the patient-specific anatomical structure allows a tangible manipulation and interaction of the anatomical structure and of the representation of the interventional tool. Nonetheless, neither fragmentation, such as for example cutting a printed organ, nor destructive steps, such as for example stent deployment, may be required. Reusability can be achieved thanks to a virtual model of the anatomical structure, such as digital biophysics organ model, where one or more functional and destructive steps can be performed, being then reversible and archived. A tracking device, such as a 3D camera or based on a magnetic tracker, is provided and configured to track a position of a physical representation of an interventional tool and the physical model of the anatomical structure. Thereby, a link between both the real-world physical model of the anatomical structure and the real-world physical representation of the interventional tool can be established. The real-world physical model of the anatomical structure is registered with the virtual model of the anatomical structure. The real-world physical representation of the interventional tool is registered with the virtual representation of the interventional tool. This can be performed by either tracking the physical model of the anatomical structure and the physical representation of the interventional tool independently or relatively to one another. In particular, the registration can be performed based on capturing the relative position of the representation of the interventional tool with respect to the physical model of the anatomical structure. The registration can be performed based on an interaction of the representation of the interventional tool with the physical model of the anatomical structure.

Hence, a specific solution for use in patient-specific intervention planning is proposed. It has been recognized that by the selective combination of a haptic real-world patient-specific physical model and a real-world representation of an interventional tool, patient-specific surgical procedures may be effectively trained in the motor cortex of the physician. An advantageous training effect can be achieved by providing the physician with feedback on his interaction. However, instead of e.g. actually cutting the physical model, such feedback may be presented based on a visualization of the virtual model of the anatomical structure and the interventional tool. Thereby, it is not necessary to provide an actually bleeding fluid-filled printed organ model connected to a pumping system. Moreover, a virtual model can provide functional information of the anatomical structure that can go beyond purely physical models, such as blood flow inside vessels, electrical current in muscles, heat transfer. The combination of both real and virtual representation of the anatomical structure can allow allows the integration of functional information that can be either too expensive to obtain in reality or unfeasible.

For example, the integration of electrical pathways in a printed heart model is currently unfeasible since the printing capabilities should be able to accurately define the anisotropy of the electrical conductivity of the material (that defines the pathways). Moreover, it would be desirable to determine the effect of a discharge of an electric current in a given position in the printed organ or another physical model of the anatomical structure. The combination of a physical model with a virtual model can provide means to measure/visualize the electrical current to be provided in the anatomical structure. As a further example, if ablation is performed as intervention, then the electric pathways should be modifiable. As a further example, in the case that physical model may contains a blood-like fluid, which may optionally be energized by a pump system, the virtual representation can be used to replace the fluid and the pump system. A further advantage can be that interactions that were done by an experienced practitioner can be automatically repeated or replayed for training.

The proposed solution may allow repeatability since neither fragmentation nor destructive steps are required. It should be noted that the prior art as cited in the introductory portion follows a different approach of providing a modular design that shall allow quick removal and replacement of disposable sections.

The geometry of the anatomical structure may be extracted from medical images. The anatomical structure may be extracted using known image processing techniques. Based thereon, a physical model of the anatomical structure may be generated.

The system may also comprise the physical representation of the interventional tool and the virtual model of the physical representation of an interventional tool. The physical representation of the interventional tool and the virtual model of the physical representation of the interventional tool may depend on the anatomical structure, e.g. on the type of organ, and the type of the intervention.

The system may comprise an interface for receiving medical image data of the anatomical structure. The system may comprise a first additive manufacturing device adapted to generate the physical model of the anatomical structure based on the medical image data. The processor can be adapted to extract the patient specific model of the anatomical structure from the received medical image data.

The system may comprise an interface for receiving construction data of the physical representation of the interventional tool. The system may comprise a second additive manufacturing device adapted to generate the physical representation of the interventional tool based on the construction data. In addition or in the alternative, the first additive manufacturing device can be adapted to also provide the physical representation of the interventional tool. The first and second additive manufacturing device can be the same or different. An additive manufacturing device can be a 3D-printer. The physical model of the anatomical structure may for example be generated in an additive manufacturing process based on plastic or silicon. The physical representation of the interventional tool may for example be generated by metal sintering. Thereby, a user may experience similar haptics to an actual surgical instrument.

The system can be configured to visualize a manipulation of the anatomical structure with the interventional tool based on tracking a position of the physical representation of the interventional tool with respect to the physical model of the anatomical structure with the tracking device, wherein said manipulation is visualized as a virtual manipulation of the virtual model of the anatomical structure. The system can comprise a screen and the visualization can be presented on said screen. Thy system can comprise glasses such as augmented reality glasses to superimpose the virtual and physical models of the anatomical structure and/or of the interventional tool. Thereby a merged view can be offered to the user. Physical interactions of the user can be rendered with their consequences in modifying the output of the virtual model. By performing certain manipulation/gestures on the printed organ with the interventional tool representation, the system can interpret that information and perform specific tasks related to the intervention. For example, if the interventional tool is an ablation catheter, then the user can indicate on the printed organ where he/she wants to ablate. For example, when the physician indicates via the physical representation of the interventional tool that an incision shall be made at a certain location of the anatomical structure, the physical model may not actually be cut. Instead, a consequence of the interaction such as bleeding can be visualized using the virtual model. An advantage can be that all functional and destructive steps may be reversible. Performed treatments can be archived e.g. as best case examples for successful treatment approaches or for comparison of different suggested treatments.

The physical representation of the interventional tool can be a dummy of the interventional tool. More precisely, the physical representation of the interventional tool can be a non-functional dummy of the interventional tool. The interventional tool can be a destructive interventional tool, in particular a scalpel (surgical knife) or electrocauter, wherein the physical representation of the interventional tool can be a non-destructive mock-up of the destructive interventional tool. For example, an intervention may require to cut an organ with a scalpel. In this case, in the physical world, the physical representation of the scalpel may be a scalpel but without blade or with a blunt blade or simply a plastic object with the shape of the scalpel (an avatar of the tool), a globe with marks or even a user's hand or finger. However, in the virtual world, the interventional tool can be a digital representation of the scalpel, which is adapted to virtually cut the digital biophysical organ, i.e., the virtual model of the anatomical structure and a respective visualization can be shown.

The virtual model of the anatomical structure can be a biophysics organ model and the system can be configured to visualize a functional behavior of the anatomical structure based on the biophysics organ model. The biophysics organ model can be adapted to virtually simulate the behavior of the patient-specific anatomical structure. The virtual or digital biophysics organ model can be indicative of a functionality in particular a dynamic functionality or behavior of the anatomical structure, e.g. pulsating vessels or a beating heart. For example, it may simulate a blood flow and thereby alleviate the need for an experimental physical setup e.g. including a pumping system that mimics blood flow in printed physical organ models as indicated in the introductory section. Additional complex phenomena can be simulated like blood coagulation, contrast injection or the modelling of the x-ray acquisition chain.

In a refinement, the system can be configured to visualize a blood flow in the anatomical structure based on the biophysics organ model.

In addition or in the alternative, the system can be configured to modify a property of the biophysics organ model, in particular to change a cardiac frequency or a visualization thereof. The property of the biophysics organ model may be modified in response to a manipulation of the anatomical structure with the interventional tool. In particular, the property of the biophysics organ model may be modified in response to a manipulation of the anatomical structure with the interventional tool based on tracking a position of the physical representation of an interventional tool and the physical model of the anatomical structure with the tracking device, in particular based on tracking a position or transient position or position path of the position of the physical representation of the interventional tool with respect to the physical model of the anatomical structure with the tracking device.

The tracking device can comprise a camera, in particular a 3D camera. In addition or in the alternative the tracking device can comprise an electromagnetic sensor adapted to determine a position of an electromagnetic marker of at least one of the physical model of the anatomical structure and the physical representation of the interventional tool. An electromagnetic marker can also refer to a magnetic marker or an electronic marker. It is also possible to use optical markers in combination with a camera-based tracking device. The marker may be placed temporarily on the physical model of the anatomical structure, e.g. on a printed organ. This can enable more reliable tracking. The tracking device may extract a position of the physical representation of the interventional tool and the physical model of the anatomical structure. This can be based on images acquired by one or more cameras comprised in the tracking device. Tracking a position of the physical representation of the interventional tool and the physical model of the anatomical structure may refer to determining an absolute position of the physical representation of the interventional tool and/or the physical model of the anatomical structure or may refer to tracking a refer to a relative position, i.e. a position of the physical representation of the interventional tool with respect to the physical model of the anatomical structure.

Accordingly, the physical model of the anatomical structure may comprise a marker, in particular an electromagnetic marker, for tracking a position of the physical model of the anatomical structure. In particular, a plurality of markers can be placed on different locations of the anatomical structure. The same holds for the physical representation of the surgical tool. This can enable more reliable tracking.

Different types of medical data may be used for determining the physical and/or virtual model pf the anatomical structure. In particular, the medical image data may comprise at least one of CT, MRI or ultrasound data of the patient.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
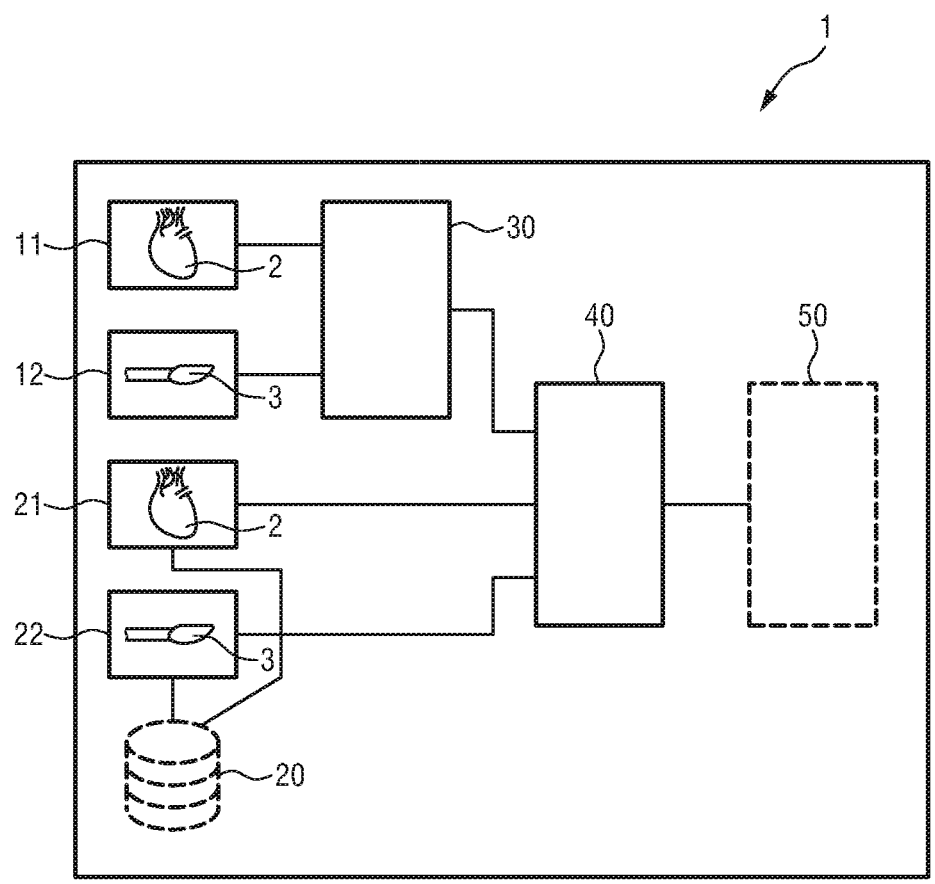
FIG. 1 shows a first exemplary embodiment of a system for a patient-specific intervention planning according to an aspect of the present disclosure.

FIG. 1 shows an embodiment of a system for a patient-specific intervention planning. The system is therein denoted in its entirety with reference numeral 1.

The system comprises a physical model 11 of an anatomical structure 2, wherein the physical model is a patient-specific physical model created based on medical image data. The system 1 further comprises a virtual model 21 of the anatomical structure 2, wherein the virtual model is a patient-specific model based on medical image data. As shown in FIG. 1, the system can comprise a database 20 that stores the virtual model 21 of the anatomical structure 2. The database can be any suitable type of storage, e.g. as a computer-readable storage medium or a data storage or database at a remote location including but not limited to a cloud-base service.

The system further comprises a tracking device 30 configured to track a position of the physical model 11 of the anatomical structure 2 as well as a position of the physical representation 12 of an intervention tool 3. The interventional tool 3 can for example be a surgical knife or scalpel, a wire, a stent or a physician's hand. It should be noted that the physical representation of the interventional tool is not necessarily part of the system 1. It can be sufficient that the tracking device 30 can track a position of the physical representation of the interventional tool. A virtual representation 22 of the interventional tool 3 can be provided. Similar to the virtual model 21 of the anatomical structure 2, the virtual representation 22 of the interventional tool 3 can be stored in the storage 20. The storage 20 can be part of the system. The system can comprise an interface for receiving the virtual model 21 of the anatomical structure 2 and the virtual representation 22 of the interventional tool 3.

The system 1 further comprises a processor 40. The processor 40 is connected to the tracking device 30. The processor can be configured to perform the steps of registering the physical model 11 of the anatomical structure 2 with the virtual model 21 of the anatomical structure 2 and registering the physical representation 12 of the interventional tool 3 with a virtual representation 22 of the interventional tool 3 based on the position of the physical representation 12 of the interventional tool 3 with respect to the physical model 11 of the anatomical structure 2. In particular, the processor 40 can be configured to perform the registration based on an interaction of the physical representation 12 of the interventional tool 3 with the physical model 11 of the anatomical structure 2.

The system 1 can further comprise a display device 50 such as a monitor or glasses comprising a display such as augmented reality glasses that can be worn by a physician. The system 1 can be configured to visualize a manipulation of the anatomical structure 2 with the interventional tool 3 based on tracking a position of the physical representation 12 of the interventional tool 3 with respect to the physical model 11 of the anatomical structure 2 with the tracking device 30. The manipulation can be visualized on the display 50 as a virtual manipulation of the virtual model 21 of the anatomical structure 2 with the virtual representation 22 of the interventional tool 3. The virtual model of the anatomical structure can also be referred to as a digital biophysics model.

In an embodiment, the proposed solution can combine a printed organ model as the physical model of the anatomic construction with a digital biophysics model as the virtual model of the anatomical structure for patient-specific interventional planning. In a first step, the geometry of an organ of interest can be extracted for medical images by processing techniques. The geometry can be turned into a physical model e.g. by 3D printing for allowing a visually tangible manipulation and interaction of the organ and interventional tools. The extracted geometry may also serve to define the domain of a biophysics organ motion or deformation, electric wave action and propagation. An exemplary application scenario is modelling of the human heart.

The proposed solution may thereby provide a cost-effective and viable alternative to the tedious path of providing a functional printed organ which may be very challenging and expensive to produce and may only provide limited re-usability.

In an example, both printed organ via a physics model can be registered in space for example by cameras or magnetic trackers. Moreover, a real object representing an interventional tool can also be registered from the real world to the digital space by means of the tracking device and registration performed by the processor 40. Hence, a mix-reality solution can be provided for merging printed organs with a biophysics model. An exemplary virtual model of the human heart currently developed by Dassault Systémes, Nafems Benchmark July 2015, Technology to transform lives: The SIMULIA Living Heart Model by Karl D. Souza.

It has been found that the proposed solution can be advantageous since it combines a hand-on experience of physician in preparation of patient-specific interventions but may at the same time provide an indication of what an outcome of different treatments and manipulations may be.

For example, the proposed mixed-reality approach is not limited by material constraints for manufacturing of the physical model of the anatomical structure but may also consider e.g. electrical and thermal conductivities by means of the virtual model of the anatomical structure and its underlying biophysics model. Hence, a more meaningful training and patient-specific intervention planning may be achieved. This may further increase the first-time-right surgical success rate.

Figure 2:
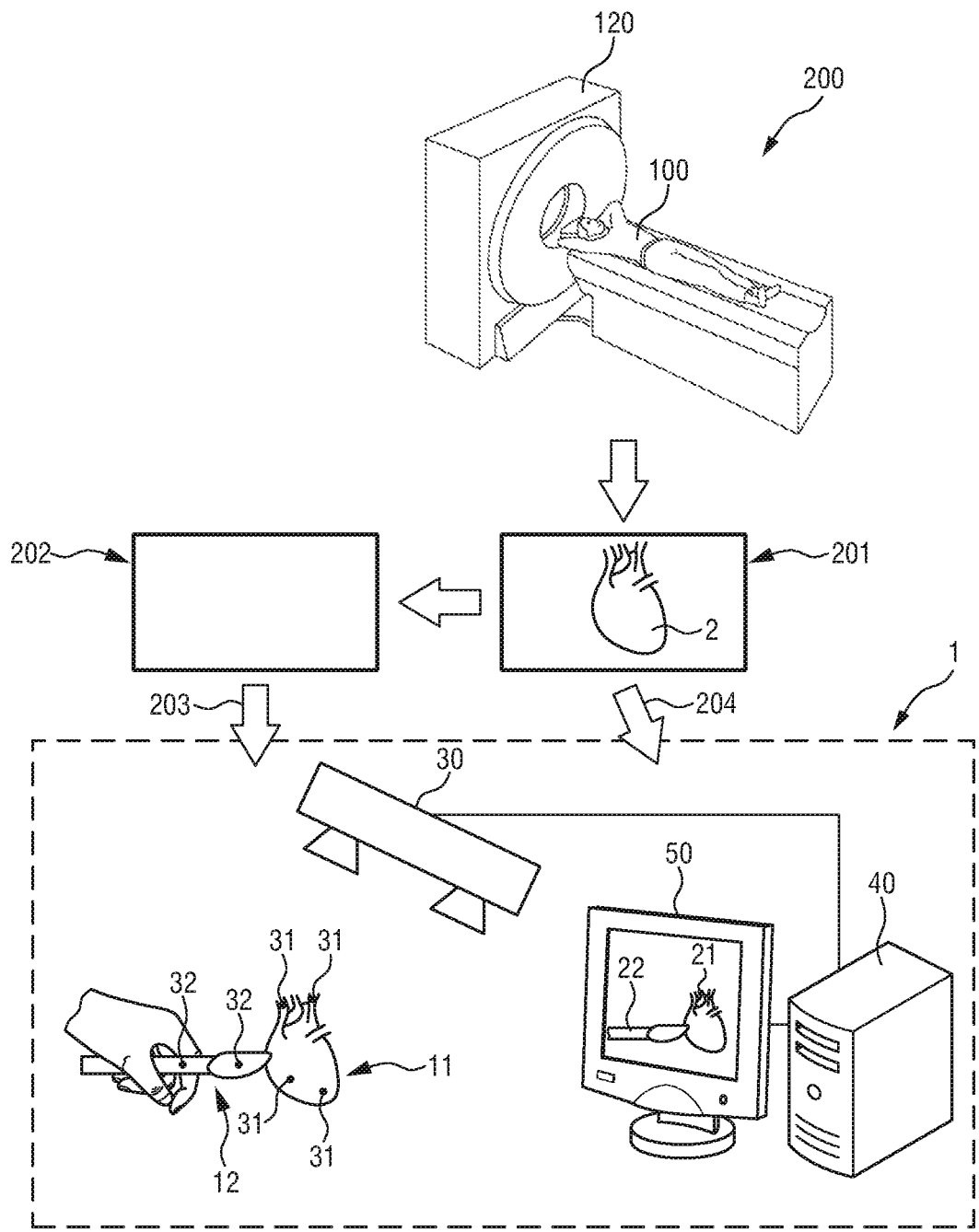
FIG. 2 shows a second exemplary embodiment of a system for a patient-specific intervention planning according to an aspect of the present disclosure.

FIG. 2 shows a more detailed example of a system for a patient-specific intervention planning including acquisition of medical images and preprocessing to obtain the physical model of the anatomical structure and the virtual model of the anatomical structure.

Medical image data can be obtained by different modalities. In the example shown in FIG. 2, a computer tomography (CT) scanner is provided. However, it is also possible to use other image acquisition modalities such as magnetic resonance imaging (MRI) or ultrasound. In the example shown in FIG. 2, a CT scanner 120 obtains 3D medical image data of a patient 100.

In FIG. 2, the medical image acquisition is denoted by reference numeral 200. From the acquired medical image data, a digital representation of the anatomical structure of interest can be extracted in step 201. In the given example, the anatomical structure of interest is a human heart 2. The extracted data can now be used to manufacture a physical, i.e. a real-world model of the anatomical structure in step 202. Optionally, the system 1 may comprise an additive manufacturing device such as a 3D printer adapted to generate the physical model 11 of the anatomical structure 2 based on the medical image data. The system 1 can comprise an interface for receiving medical image data of the anatomical structure. Optionally, the system 1 may also comprise an interface for receiving construction data of the physical representation 12 of the interventional tool 3. The same or a different additive manufacturing device may be provided to generate the physical representation of the interventional tool based on the construction data.

An advantage of this embodiment is that easy access to different interventional tools can be provided. For example, different interventional tools may be expensive and may not be necessarily be available at a certain hospital. To overcome this limitation, the hospital may only need to print the anatomical structure and may print and test digital representations of one or more different interventional devices of interest, without the need of physically acquiring them. The digitalization of the devices can be important when multiple alternatives are available on the market. Testing a device digitally can save cost and time and may lower the bar for using further improved technology.

In the example shown in FIG. 2, a 3D camera is provided as a tracking device 30. The 3D camera can acquire 3D images of a scenery. Thereby, the tracking device 30 can track a position of the physical representation 12 of the interventional tool with respect to the physical model 11 of the anatomical structure.

Optionally, the physical model 11 of the anatomical structure can comprise one or more markers 31 for tracking a position of the physical model 11 of the anatomical structure. Thereby, a tracking accuracy can be improved. In addition or in an alternative embodiment, the tracking device 30 can comprise a sensor adapted to determine a position of a magnetic marker 31 on at least one of the physical model 11 of the anatomical structure and the physical representation 12 of the interventional tool. Accordingly, the physical model of the anatomical structure 11 can be provided with a marker 31 being an electromagnetic marker. The electromagnetic marker can refer to an electronic or magnetic marker such as a magnet, or such as a RFID tag. Tracker may be permanently or temporarily applied. The printed organ and real interventional tool can have specific printed landmarks to facilitate their registration and tracking.

It should be noted that in some instances, a physician may also perform manipulations of an anatomical structure with his hands. Hence, a physical representation of interventional tool is not limited to separate tools such as wires, surgical knives, stents and the like but may also refer to for example the surgeon's hands, which can also be tracked and a virtual representation thereof can be established.

Referring again to FIG. 2, the processor 40 can be adapted to register the physical representation of the anatomical structure, here the printed organ model, and the corresponding virtual model of the anatomical structure extracted from the image data in step 201. As shown in FIG. 2, a virtual or digital representation 22 of the interventional tool can also be registered in the same way of registering the physical model of the anatomical structure.

In an example shown in FIG. 2, there is provided a screen 50 to visualize a manipulation of the anatomical structure with the interventional tool based on tracking a position of the physical representation of the interventional tool with respect to the physical model of the anatomical structure with the tracking device 30. In addition or in the alternative, augmented reality glasses can be provided such that both physical and virtual objects and/or physical and virtual presentations of the surgical tool can be superimposed. Thereby, a merged view can be offered to the user.

By performing certain manipulations/gestures on the physical representation 11 of the anatomical structure with the physical representation 12 of the interventional tool, the processor can interpret that information and perform specific tasks related to the intervention. For example, if the interventional tool is a catheter then the user can indicate on the printed organ where he/she wants to ablate. The following examples are presented to illustrate examples how to use the present disclosure:

Example (1)—Device deployment for arteries: If the anatomical structure is artery with a stenosis (or an aneurysm), the intervention can be the deployment of an endovascular device, such as a stent. In this case, the physical representation of the interventional tool can be a wire to mimic a catheter which will be the virtual representation of the interventional tool. The user can then perform specific gestures to move the interventional tool, more precisely to move the physical representation of the interventional tool with respect to the physical model of the anatomical structure, to virtually deploy the stent inside the digital biophysics model, i.e. the virtual model of the anatomical structure. Optionally, in the virtual model of the anatomical structure, blood flow can be circulating and/or contrast injection can be virtually performed, while manipulating the physical model of the anatomical structure and the physical representation of the interventional tool.

Example (2)—Atrial ablation: If the anatomical structure is a heart and atrial ablation is the chosen therapy, then the physical representation of the interventional tool can reproduce the behavior of the ablation catheter. The virtual model or digital biophysics model can be configured to provide an electrical wave activation and propagation in the heart that is adapted to change while the user burns specific areas of the heart. The areas to burn can be indicated in the physical model of the anatomical structure with the physical representation of the interventional tool by the user. The virtual model of the heart can also beat, if required.

Example (3) Surgery for congenital heart diseases: If tissue removal and suturing are required, the physical representation of the interventional tool can be the hand of the physician, an object to represent a surgical knife and stitches or biocompatible patches. For cutting, the user may perform specific gestures using the physical representation of the interventional tool to indicate where he/she wants to cut the anatomical structure. It should be noted that a cut can be done virtually in the virtual model of the anatomical structure. If a disconnected piece of tissue is being used after cutting, then the piece may move with gestures. To indicate in the physical model of anatomical structure that the piece does not exist after removal in the virtual model, it is possible to use augmented reality glasses. For example, non-removed pieces in the physical model that have been removed in the virtual model can be indicated with a different color or transparency to indicate the part that was digitally removed. When the user wants to merge to disconnected pieces, he/she can use the physical model of the anatomical structure to identify the merging points and perform suing or patching in the virtual model of the anatomical structure.

An advantage of the proposed solution can be that it is possible to undo steps and/or to store steps for further analysis for teaching purposes. Due to the portability of all elements, a physical model of an anatomical structure can be printed in several locations at the same time for multiple evaluations. Moreover, a specialist may train an intervention several times, optionally at a remote location before flying in for actual surgery.

In a further refinement, the virtual model of the anatomical structure can be a biophysics organ model and the system can be configured to visualize a functional behavior of the anatomical structure based on the biophysics organ model. For example, the system can be configured to visualize a blood flow in the anatomical structure based on the biophysics organ model. Optionally, it is also possible to change a parameter of the biophysics organ model, in particular to change a cardiac frequency and a visualization thereof to make a more realistic simulation and to see how users can react to these events. This is in particular advantageous for teaching. The parameter can be changed in response to a manipulation of the anatomical structure with the intervention tool based on tracking a position of the physical representation of the interventional tool with respect to the physical model of the anatomical structure with the tracking device.

Figure 3:
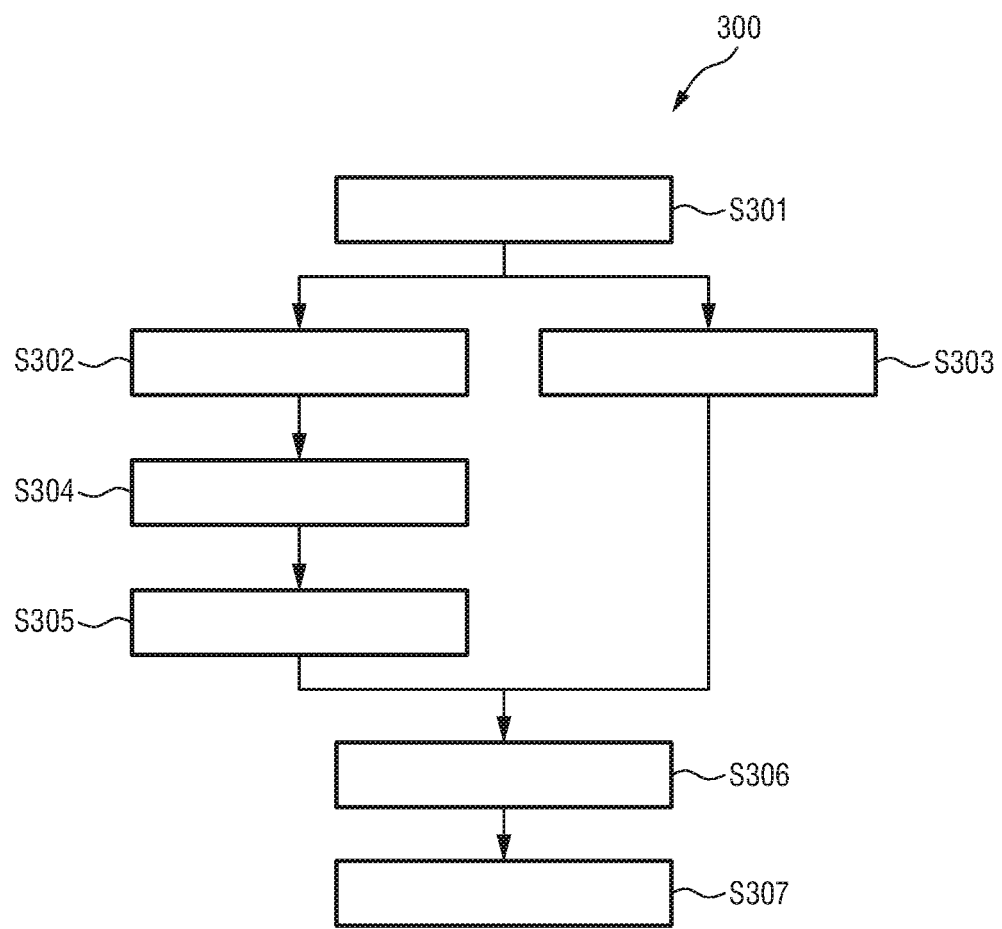
FIG. 3 shows a flowchart of a method for a patient-specific intervention planning according to an aspect of the present disclosure.

FIG. 3 shows an exemplary flow chart of a method for patient-specific intervention planning. In a first step S301, medical image can be received. In a second step S302, a physical model of the anatomical structure may be generated, wherein the physical model is a patient-specific model, based on the medical image data.

In a step S303, which may be performed before after or in parallel of one or more of the steps S302, S304 and S305, a virtual model of the anatomical structure may be generated or determined, wherein the virtual model is a patient-specific model based on the medical image data.

In step S304, a physical representation of an interventional tool can be provided. In step S305, a position of the physical representation of the interventional tool can be tracked with respect to the physical model of the anatomical structure.

In step S306, the real-world path via steps S302, S304 and S305 may be merged with the virtual-world by registering the physical model of the anatomical structure with the virtual model of the anatomical structure and registering the physical representation of the interventional tool with a virtual representation of the interventional tool based on the position of the physical representation of an interventional tool with respect to the physical model of the anatomical structure. In step S307, a visualization of the virtual representation of the interventional tool and/or the virtual model of the anatomical structure may be presented, in particular in response to manipulation of the anatomical structure with the interventional tool.

Figure 4:
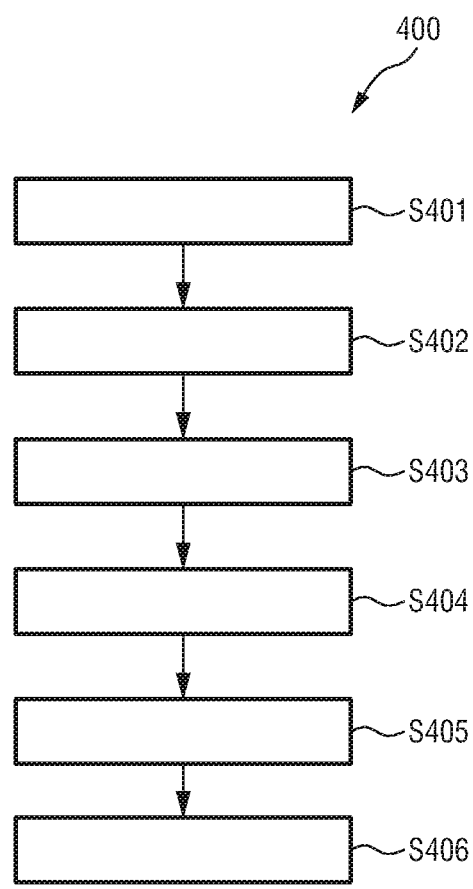
FIG. 4 shows a flowchart of method steps of a computer program.

FIG. 4 shows an exemplary flow chart of a computer program comprising program code means for causing a computer to carry out the following steps when said computer program is carried out on a computer. In step S401 medical image data is received. In step S402, a digital representation of a physical model of an anatomical structure is generated, wherein the physical model is a patient-specific model, based on the medical image data. The digital representation of the physical model can for example be data for causing a 3D printer to generate the physical model of the anatomical structure. In step S403, a virtual model of the anatomical structure is generated, wherein the virtual model is a patient-specific model based on the medical image data. For example, the virtual model can be a virtual biophysics model.

In step S404, position data indicative of a position of the physical representation of the interventional tool with respect to the physical model of the anatomical structure is received. In step S405, the physical model of the anatomical structure is registered with the virtual model of the anatomical structure and the physical representation of the interventional tool is registered with a virtual representation of the interventional tool based on the position data indicative of the position of the physical representation of an interventional tool with respect to the physical model of the anatomical structure.

In step S406, visualization data can be generated to provide a visualization of the virtual representation of the interventional tool and/or the virtual model of the anatomical structure, in particular in response to manipulation of the anatomical structure with the interventional tool.

In conclusion, a further improved system and method for use in patient specific interventional planning have been presented. The proposed solutions may assist in planning and training interventions that can be adapted to the specific patient. Thereby, the present disclosure may help to increase the first-time-right surgical success.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for patient-specific intervention planning, the system comprising:
    a physical model of an anatomical structure, wherein the physical model is a patient-specific model based on medical image data;
    a virtual model of the anatomical structure, wherein the virtual model is a patient-specific model based on medical image data;
    a tracking device configured to track a position of a physical representation of an interventional tool and the physical model of the anatomical structure;
    a processor configured to perform the step of:
        registering the physical model of the anatomical structure with the virtual model of the anatomical structure such that a manipulation to the physical model is depicted virtually, and registering the physical representation of the interventional tool with a virtual representation of the interventional tool based on the position of the physical representation of the interventional tool and the physical model of the anatomical structure.

2. The system of claim 1, further comprising:
    an interface for receiving medical image data of the anatomical structure; and
    a first additive manufacturing device adapted to generate the physical model of the anatomical structure based on the medical image data.

3. The system of claim 1, further comprising:
    an interface for receiving construction data of the physical representation of the interventional tool; and
    a second additive manufacturing device adapted to generate the physical representation of the interventional tool based on the construction data.

4. The system of claim 1, wherein said manipulation of the physical model of the anatomical structure with the physical representation of the interventional tool is visualized as a virtual manipulation of the virtual model of the anatomical structure based on tracking the position of the physical representation of the interventional tool and the physical model of the anatomical structure with the tracking device.

5. The system of claim 1, wherein the physical representation of the interventional tool is a dummy of the interventional tool.

6. The system of claim 1, wherein the interventional tool is a destructive interventional tool, in particular a scalpel or electrocauter, wherein the physical representation of the interventional tool is a non-destructive mock-up of the destructive interventional tool.

7. The system of claim 1, wherein the virtual model of the anatomical structure is a biophysics organ model and wherein a functional behavior of the anatomical structure based on the biophysics organ model is visualized on the virtual model.

8. The system of claim 7, wherein a blood flow in the anatomical structure based on the biophysics organ model is visualized on the virtual model.

9. The system of claim 7, wherein property of the biophysics organ model is modified, in particular to change a cardiac frequency of a visualization thereof, in response to a manipulation of the anatomical structure with the interventional tool based on tracking the position of the physical representation of the interventional tool with respect to the physical model of the anatomical structure with the tracking device.

10. The system of claim 1, wherein the tracking device comprises a 3D camera.

11. The system of claim 1, wherein the tracking device comprises a magnetic sensor adapted to determine a position of a magnetic marker of at least one of the physical model of the anatomical structure and the physical representation of the interventional tool.

12. The system of claim 1, wherein the physical model of the anatomical structure comprises a marker, in particular an electromagnetic marker, for tracking a position of the physical model of the anatomical structure.

13. The system of claim 1, wherein the medical image data comprises at least one of CT, MRI or ultrasound data of the patient.

14. Method for patient-specific intervention planning, the method comprising:
- receiving medical image data;
- generating a physical model of an anatomical structure, wherein the physical model is a patient-specific model, based on the medical image data;
- generating a virtual model of the anatomical structure, wherein the virtual model is a patient-specific model based on the medical image data;
- providing a physical representation of an interventional tool;
- tracking a position of the physical representation of the interventional tool and the physical model of the anatomical structure; and
- registering the physical model of the anatomical structure with the virtual model of the anatomical structure such that a manipulation to the physical model is depicted virtually, and registering the physical representation of the interventional tool with a virtual representation of the interventional tool based on the position of the physical representation of an interventional tool and the physical model of the anatomical structure.

15. A non-transitory computer-readable medium storing computer-executable instructions for performing a method of running a computer program on a computing device comprising program code means for causing a computer to carry out the following steps when said computer program is carried out on the computing device;
- receiving medical image data;
- generating a digital representation of a physical model of an anatomical structure, wherein the physical model is a patient-specific model, based on the medical image data;
- generating a virtual model of the anatomical structure, wherein the virtual model is a patient-specific model based on the medical image data;
- receiving position data indicative of a position of the physical representation of the interventional tool and the physical model of the anatomical structure; and
- registering the physical model of the anatomical structure with the virtual model of the anatomical structure such that a manipulation to the physical model is depicted virtually, and registering the physical representation of the interventional tool with a virtual representation of the interventional tool based on position of the physical representation of an interventional tool and the physical model of the anatomical structure.

* * * * *